Dec. 11, 1934. L. PAHISSA Plant Pat. 116
ROSE
Filed July 26, 1934
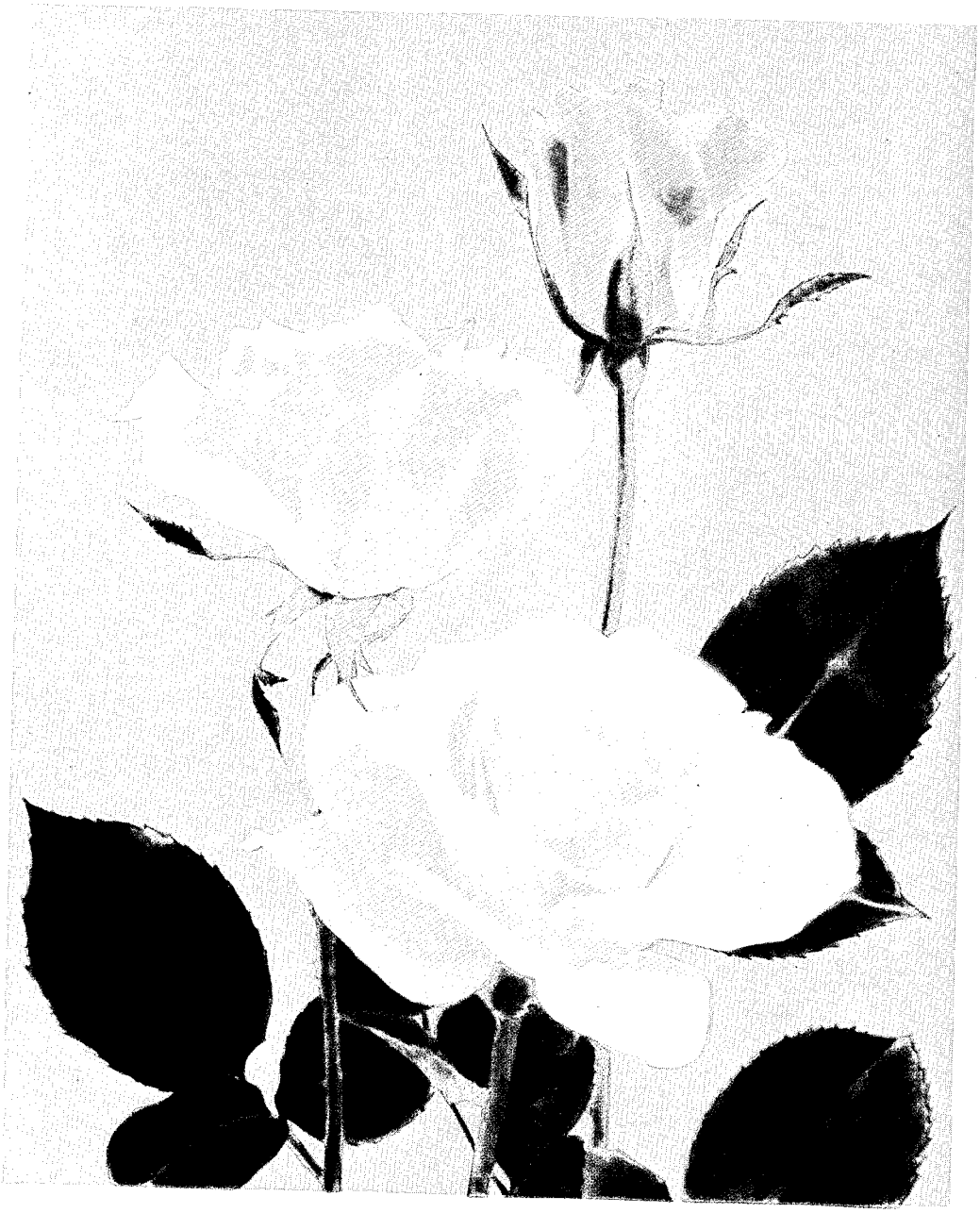
Inventor
Lorenzo Pahissa
By Robb & Robb
attorneys Patented Dec. 11, 1934

UNITED STATES PATENT OFFICE

116

ROSE

Lorenzo Pahissa, San Feliu de Llobregat, Spain, assignor to Jackson & Perkins Company, Newark, N. Y., a corporation of New York Application July 26, 1934, Serial No. 737,123

1 Claim. (Cl. 47—61)

The present invention relates to an improved rose plant having as its objective a blending including the two strains of Rosa foetida by means of which to impart to the progeny the ruggedness and hardiness of that species and at the same time to combine the colors to produce a rose of novel coloring.

In the successful attainment of this objective I have found that this new variety has inherited in equal proportions all the desirable features of the ancestors, producing a great improvement over the existing run of garden roses.

The color of the bloom of this origination is a new departure not previously known in the class generally described as "Hybrid Teas".

Extensive tests have demonstrated that this new rose responds well to forcing treatment particularly in a greenhouse and bids fair to become a popular variety in the cut-flower market.

One of the important features of the present invention resides in the fact that the flowers come in rapid succession and in great quantity throughout the vegetative season, adding materially to its value as a garden rose as well as a commercial cut-flower variety.

A further important feature is found in the foliage of the plant which is exceptionally strong and healthy and may be considered as approaching immunity from the ordinary ills to which the average Hybrid Tea is subject under average garden conditions.

The following is a description of the plant from which two important features of distinctness may be said to stand out, to wit: the newness of the color of the blossom and the great hardiness and disease resistance characteristics of the plant as a perpetual flowering garden rose.

The color standard used herein is the Gravereaux system, except where indicated by asterisk which refers to the standard dictionary definition.

Parentage:—
Seedling.
*Seed parent.*—Angele Pernet.
*Pollen parent.*—Comtesse de Castilleja.

Classification:—
*Botanical.*—Hybrid Tea with some Austrian Briar ancestry.
*Commercial.*—Hybrid Tea.

*Flower*

Blooming habit:—
Observations made at various places.
*Recurrent.*—Continuous.
*Quantity.*—Profuse.

Bud:—
*Size.*—Large.
*Form.*—Urn.
Not affected by wet weather.
Not affected by hot weather.
*Color.*—When sepals first divide, deep, dark reddish brown; when petals begin to unfurl, lightening to sorrel* or yellowish brown; when half blown, inside of petals, rich apricot; reverse of petals, sorrel* striated with yellow veins.
*Sepals.*—Branched; "hood" above bud. Stand up.
*Calyx.*—Shape—funnel. Size—long. Aspect—smooth. Odor when rubbed—russet apple.
*Peduncle.*—Length—long. Aspect—smooth. Color—green. Strength—erect, heavy.
*Opening.*—Opens well. Not affected by adverse conditions.

Bloom:—
*Size.*—Large. Average size when fully expanded 4½ inches.
*Borne.*—Singly.
*Stems.*—Long, strong.
*Form.*—When first open, cupped. Permanence—flattens; outer petals curl back.
*Petalage.*—Double (full but open center). Number of petals under normal conditions 30 to 40.
*Color.*—Center of flower deep apricot, around a yellow circle. Outer petals, sorrel*. Base of petals (aiglet), yellow. Inside of petals, deep apricot. Reverse of petals, sorrel*. General tonality from a distance, light sorrel*.
*Variegations.*—Penciled or veined-yellow veins running herringbone fashion.
*Discoloration.*—General tonality at end of first day apricot to sorrel*. Second day—slightly lighter sorrel*. Third day—brilliant orange coral.

Petals:—
*Texture.*—Thick, unaffected by wet or hot weather.
*Appearance.*—Inside—satiny. Outside—shiny.
*Form.*—Round.
*Arrangement.*—Imbricated (regularly arranged shinglelike). Petaloids in center; few, large.
*Persistence.*—Drop off cleanly.
*Fragrance.*—Moderate. Nature—fruity (russet apple).
*Lastingness.*—On the plant, very long. As cut flower, very long.

Genital organs:—
*Stamens, anthers.*—Medium size, many. Color—yellow. Arrangement—regular around styles.

*Stamens, filaments (threads).*—Long. Color—white.

*Pollen.*—Lemon yellow.

*Styles.*—Bunched, even length; medium; heavy.

*Stigmas.*—Color—white.

*Ovaries.*—All enclosed in calyx.

Fruit:—

Variety is fertile with its own pollen.

*Form.*—Round, depressed top, seeds protruding at times.

*Aspect.*—Smooth.

*Color at maturity.*—Orange.

*Sepals.*—Caducous (soon falling).

*Plant*

Form:—

Bush.

Growth:—

Very vigorous; upright; branching.

Foliage:—

Generally 5, sometimes 7 leaflets.

*Size.*—Medium.

*Quantity.*—Abundant.

*Color.*—New foliage: upper side, dark green and bronzy. Under side, bronzy. Old foliage: upper side, very dark green. Under side, dark green.

*Shape.*—Oval pointed.

*Texture.*—Upper side—glossy. Under side—rough. Ribs and veins—ordinary.

*Edge.*—Serrated (saw toothed).

*Serration.*—Single; large, sharp.

*Leaf stem.*—Color, green. Under side—prickles.

*Stipules.*—Medium, smooth.

*Disease resistance.*—Resistant.

Wood:—

*New Wood.*—Color, light green. Bark—rough.

*Old Wood.*—Color, green. Bark—smooth.

Thorns.—(N. B.—Thorns are divided into thorns, prickles and short needles.)

*Thorns.*—Quantity: On main stalks from base, few. On laterals from stalk, ordinary. Form—broad base, medium length, straight. Color when young—red. Position—irregular.

*Prickles.*—Quantity: On main stalks, few. On laterals, few. Color—brown.

*Short Needles.*—Quantity: On main stalks, none. On laterals, none.

This variety has been asexually reproduced for several generations and is now a fixed type coming true to form by asexual propagation.

I claim:—

A new and distinct variety of Hybrid Tea rose plant characterized by its great hardiness and disease resistance, as described, and the combination sorrell* and apricot coloring of its flower, as shown.

LORENZO PAHISSA.